United States Patent
Adesuyi et al.

(10) Patent No.: US 10,946,015 B2
(45) Date of Patent: *Mar. 16, 2021

(54) STABLE PHARMACEUTICAL COMPOSITIONS COMPRISING A PYRIMIDINE-SULFAMIDE

(71) Applicant: ACTELION PHARMACEUTICALS LTD., Allschwil (CH)

(72) Inventors: Charles Tokunbo Adesuyi, Swindon (GB); Bruce Hamilton Lithgow, Bath (GB); Olivier Lambert, Spechbach-le-Haut (FR); Lovelace Holman, Arlesheim (CH)

(73) Assignee: ACTELION PHARMACEUTICALS LTD, Allschwil (CH)

( * ) Notice: Subject to any disclaimer, the term of this patent is extended or adjusted under 35 U.S.C. 154(b) by 75 days.

This patent is subject to a terminal disclaimer.

(21) Appl. No.: 15/900,586

(22) Filed: Feb. 20, 2018

(65) Prior Publication Data

US 2018/0263980 A1 Sep. 20, 2018

Related U.S. Application Data

(63) Continuation of application No. 15/002,255, filed on Jan. 20, 2016, now Pat. No. 10,117,870, which is a continuation of application No. 13/736,699, filed on Jan. 8, 2013, now Pat. No. 9,265,762, which is a continuation of application No. 12/388,142, filed on Feb. 18, 2009, now Pat. No. 8,367,685, which is a continuation-in-part of application No. 12/066,448, filed as application No. PCT/IB2006/053210 on Sep. 11, 2006, now abandoned.

(30) Foreign Application Priority Data

Sep. 12, 2005 (WO) .................. PCT/EP2005/009775

(51) Int. Cl.
*A61K 31/506* (2006.01)
*A61K 9/16* (2006.01)
*A61K 9/20* (2006.01)
*A61K 9/28* (2006.01)

(52) U.S. Cl.
CPC .......... *A61K 31/506* (2013.01); *A61K 9/1652* (2013.01); *A61K 9/205* (2013.01); *A61K 9/2059* (2013.01); *A61K 9/2077* (2013.01); *A61K 9/2846* (2013.01); *A61K 9/2866* (2013.01)

(58) Field of Classification Search
CPC .. A61K 31/506; A61K 9/2866; A61K 9/2846; A61K 9/2077; A61K 9/2059; A61K 9/205; A61K 9/1652

See application file for complete search history.

(56) References Cited

U.S. PATENT DOCUMENTS

| | | |
|---|---|---|
| 5,292,740 A | 3/1994 | Burri et al. |
| 5,733,873 A | 3/1998 | Osterberg et al. |
| 5,811,120 A | 9/1998 | Gibson et al. |
| 5,945,098 A | 8/1999 | Sarno et al. |
| 7,094,781 B2 | 8/2006 | Bolli et al. |
| 7,101,658 B2 | 9/2006 | Ohzeki et al. |
| 7,125,565 B2 | 10/2006 | Sugishita et al. |
| 7,285,549 B2 | 10/2007 | Bolli et al. |
| 7,976,869 B2 | 7/2011 | Blouquin et al. |
| 8,268,847 B2 | 9/2012 | Clozel |
| 8,367,685 B2 | 2/2013 | Adesuyi et al. |
| 8,541,433 B2 | 9/2013 | Clozel et al. |
| 8,809,334 B2 | 8/2014 | Clozel |
| 9,265,762 B2 | 2/2016 | Adesuyi et al. |
| 2001/0056183 A1 | 12/2001 | Wu et al. |
| 2002/0076436 A1 | 6/2002 | Batra et al. |
| 2004/0062803 A1 | 4/2004 | Hedden et al. |
| 2004/0076675 A1 | 4/2004 | Sugishita et al. |
| 2005/0137189 A1 | 6/2005 | Van Duzer et al. |
| 2006/0199795 A1 | 9/2006 | Itoh et al. |

(Continued)

FOREIGN PATENT DOCUMENTS

| | | |
|---|---|---|
| EP | 0747050 | 12/1996 |
| EP | 0882719 | 12/1998 |

(Continued)

OTHER PUBLICATIONS

"Polyoxyethylene Sorbitan Fatty Acid Esters", Handbook of Pharmaceutical Excipients, p. 581-584 (date of revision Aug. 22, 2005).
Ansel et al., "Capsules and Tablets", Pharmaceutical Dosage Forms and Drug Delivery Systems, 7th Edition, p. 196-209. (1999).
Banker et al., "Tablets", The Theory and Practice of Industrial Pharmacy, 3rd Edition, p. 293-345, (1986).
Banker, et al. Modern Pharmaceutics. Chapters 10 & 11. 4th ed. vol. 121, pp. 447-451, 458, 464-465, 469, 471, 548, 550, (2006).

(Continued)

*Primary Examiner* — Matthew P Coughlin
*Assistant Examiner* — Thurman Wheeler
(74) *Attorney, Agent, or Firm* — Hoxie & Associates LLC

(57) ABSTRACT

The invention relates to stable pharmaceutical compositions comprising the compound of the below formula, or pharmaceutically acceptable salts, solvates, hydrates or morphological forms thereof.

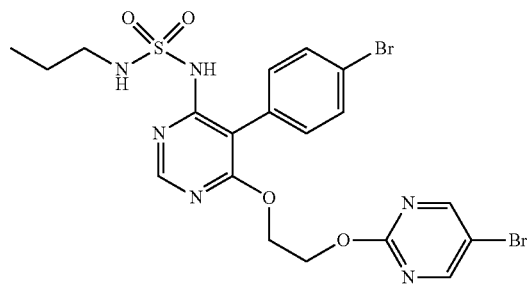

42 Claims, 6 Drawing Sheets

(56) References Cited

U.S. PATENT DOCUMENTS

| | | |
|---|---|---|
| 2008/0233188 A1 | 9/2008 | Adesuyi et al. |
| 2010/0311774 A1 | 12/2010 | Clozel |
| 2011/0136818 A1 | 6/2011 | Clozel |
| 2013/0005734 A1 | 1/2013 | Clozel |
| 2013/0310407 A1 | 11/2013 | Regenass |
| 2013/0317048 A1 | 11/2013 | Clozel et al. |
| 2014/0148460 A1 | 5/2014 | Clozel et al. |
| 2014/0329824 A1 | 11/2014 | Clozel et al. |
| 2016/0136163 A1 | 5/2016 | Adesuyi |

FOREIGN PATENT DOCUMENTS

| | | |
|---|---|---|
| JP | 4103525 A | 4/1992 |
| JP | 2001-335469 | 12/2001 |
| WO | WO 2002/000216 | 1/2002 |
| WO | WO 2002/046172 | 6/2002 |
| WO | WO 02/053557 | 7/2002 |
| WO | WO 2003/043602 | 5/2003 |
| WO | WO 2003/068235 | 8/2003 |
| WO | WO 2003/072139 | 9/2003 |
| WO | WO 2004/075894 | 9/2004 |
| WO | WO 2007/031933 | 3/2007 |

OTHER PUBLICATIONS

Collett et al., "Modified-Release Peroral Dosage Forms", Pharmaceutics—The Science of Dosage Form Design, Second Edition, Chapter 20, p. 289-305, (2002).
Cujesov, V.I., et al. "Industrial Technology of Medicaments." Charkov, Publ. NFAU, MTK-Book, vol. 2, pp. 330-334. (2002).
Fiedler, *Lexikon der Hilfsstoffe für Pharmazie, Kosmetik und angrenzende Gebiete.* 4th ed. Edito Cantor, Aulendorf. (1996).
*Hagers Handbuch der Pharmazeutischen Praxis.* $4^{th}$ ed. Springer Verlag. Berlin, Heidelberg, New York. (1971).
*Hagers Handbuch der Pharmazeutischen Praxis.* $4^{th}$ ed. Springer Verlag. Berlin, Heidelberg, New York. (1977).
Kibbe, *Handbook of Pharmaceutical Excipients, Third Edition.* American Pharmaceutical Association, Washington, D.C., USA and Pharmaceutical Press, London, UK. (2000).
Kottke et al., "Chapter 10—Tablet Dosage Forms", Modern Pharmaceutics, Fourth Edition, vol. 121, p. 287-330, (2002).
Lachman et al. *The Theory and Practice of Industrial Pharmacy.* $3^{rd}$ ed. Lea & Febiger, Philadelphia, USA. (1986).
Liberman et al., "Pharmaceutical Dosage Froms: Tablets", vol. 1, $2^{nd}$ Edition, Chapters 2, 3 and 4, Revised and Expanded, (1989).
Lieberman et al. Pharmaceutical Dosage Forms: Tablets. 2nd ed. vol. 1. (1989).
Non-Final Office Action dated May 6, 2005 regarding U.S. Appl. No. 10/433,041, (later issued as U.S. Pat. No. 7,094,781).
Ravin et al., "Preformulation", Remington's Pharmaceutical Sciences, $18^{th}$ Edition, Chapter 75, p. 1435-1450, (1990).
*Remington's Pharmaceutical Sciences.* $13^{th}$ ed. Mack Publishing Company, Easton, PA, USA. (1975).
*Remington's the Science and Practice of Pharmacy.* Part 5, "Pharmaceutical Manufacturing." Chapter 39, $21^{st}$ ed. (2005).
*Remington's the Science and Practice of Pharmacy.* Part 5, "Pharmaceutical Manufacturing." Chs. 38, 41, & 45. 21st ed. (2005).
*Remington's the Science and Practice of Pharmacy.* Part 5, "Pharmaceutical Manufacturing." p. 1072, $21^{st}$ ed. (2005).
Response and Amendment dated Aug. 3, 2012 regarding U.S. Appl. No. 12/388,142 (later issued as U.S. Pat. No. 8,367,685).
RÖMPP Online, George Thieme Verlag. Stuttgart, DE. (2007).
Rudnic et al., "Oral Solid Dosage Forms", Remington's Pharmaceutical Sciences, 18th Edition, Chapter 89, p. 1633-1675, (1990).
Specifications: Test Procedures and Acceptance Criteria for New Drug Substances and New Drug Products: Chemical Substances Q6a, International Conference on Harmonisation of Technical Requirements for Registration of Pharmaceuticals for Human Use, Federal Register, vol. 65 (251), Dec. 29, 2000.
SPh USSR 11 publ., ed. 2. "Common Methods of Analyzing Medicinal Plant Materials—Moscow." Medicina. pp. 159. (1990).
Sucker et al. *Pharmazeutische Technologie.* Georg Thieme Verlag. Stuttgart, New York. (1991).
Swinyard et al., "Pharmaceutical Necessities", Remington's Pharmaceutical Sciences, $18^{th}$ Edition, Chapter 66, p. 1313 and 1323, (1990).
Trillo et al., "Tratado de Farmacia Galenica", $1^{st}$ Edition, Chapter 5, (1993).
Niazi, Sarfaraz K., *Handbook of Pharmaceutical Manufacturing Formulations: Compressed Solid Products*, vol. 1, CRC Press, 43 pages (2004).

STABLE PHARMACEUTICAL COMPOSITIONS COMPRISING A PYRIMIDINE-SULFAMIDE

CROSS REFERENCE TO RELATED APPLICATIONS

This application is a Continuation application of U.S. application Ser. No. 15/002,255 filed on Jan. 20, 2016 which is a Continuation application of U.S. application Ser. No. 13/736,699 filed on Jan. 8, 2013, which is a Continuation application of U.S. application Ser. No. 12/388,142 filed on Feb. 18, 2009, which is a Continuation-in-Part of U.S. application Ser. No. 12/066,448 filed on Mar. 19, 2008, which is a U.S. filing under 35 U.S.C. 371 of International Application No. PCT/IB2006/53210 filed on Sep. 11, 2006, which claims the benefit of PCT/EP2005/009775 filed on Sep. 12, 2005, the contents of each of which are incorporated herein by reference.

The present invention relates to stable pharmaceutical compositions comprising propylsulfamic acid [5-(4-bromo-phenyl)-6-[2-(5-bromo-pyrimidin-2-yloxy)-ethoxy]-pyrimidin-4-yl]-amide or pharmaceutically acceptable salts, solvates, hydrates or morphological forms thereof, said compound being hereinafter referred to as the compound of formula I. The compound of formula I has the following formula:

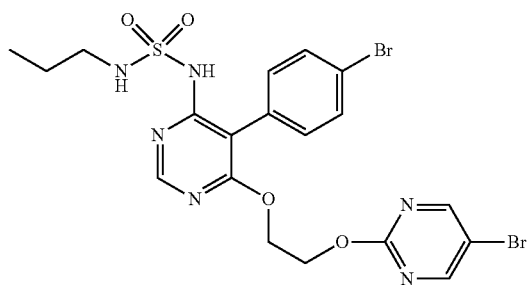 [SMILES: CCCNS(=O)(=O)Nc1ncnc(OCCOc2ncc(Br)cn2)c1-c1ccc(Br)cc1]

I

The compound of formula I is an endothelin receptor inhibitor and useful as endothelin receptor antagonist. The compound of formula I and the preparation thereof is disclosed in WO 02/053557.

Within the context of this disclosure, any reference to the compound of formula I is to be understood as referring also to the pharmaceutically acceptable salts or solvates, including hydrates, of the compound of formula I, as well as to the morphological forms thereof, if not indicated otherwise and where appropriate and expedient.

The present compound of formula I is currently being evaluated in clinical trials, thus a stable formulation had to be developed. The present invention therefore relates to stable pharmaceutical compositions comprising the compound propylsulfamic acid [5-(4-bromo-phenyl)-6-[2-(5-bromo-pyrimidin-2-yloxy)-ethoxy]-pyrimidin-4-yl]-amide, or pharmaceutically acceptable salts, solvates, hydrates or morphological forms thereof.

A stable pharmaceutical composition according to this invention will comprise:
  a) the compound of formula I having the formula shown hereafter, or a pharmaceutically acceptable salt, solvate, hydrate or morphological form thereof,

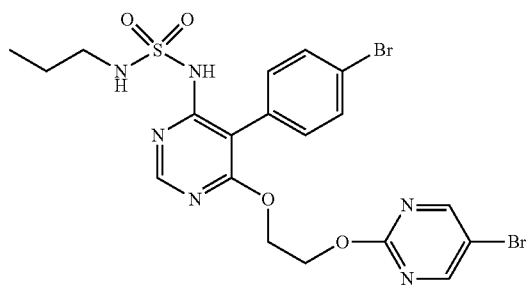 [SMILES: CCCNS(=O)(=O)Nc1ncnc(OCCOc2ncc(Br)cn2)c1-c1ccc(Br)cc1]

b) a filler,
  c) a disintegrant,
  d) a surfactant,
  e) a lubricant.

Figure 1:
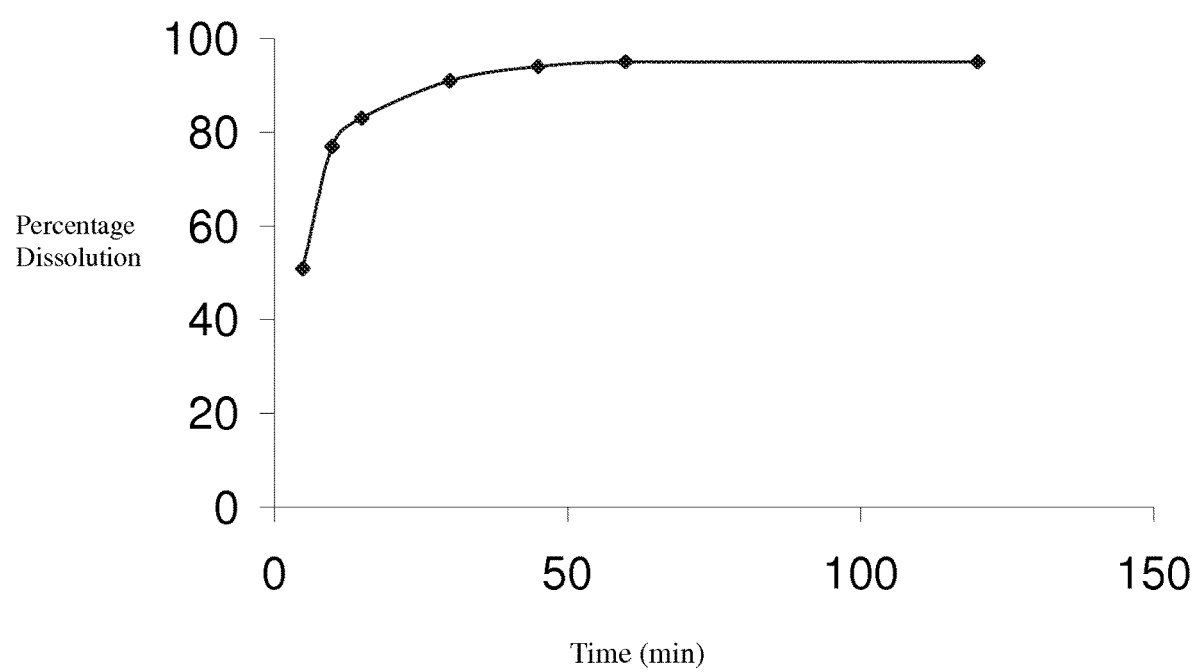
FIG. 1 shows the dissolution profile for the compositions of Examples 16-20.

According to a preferred embodiment of this invention, the pharmaceutical composition will be in the form of a tablet.

According to another preferred embodiment of this invention, the pharmaceutical composition will be in the form of a capsule.

Stable pharmaceutical compositions according to this invention will preferably be such that the filler is selected from one or more of the following: lactose, maize starch, pregelatinized starch, dibasic calcium phosphate dihydrate ($CaHPO_4.2H_2O$), microcrystalline cellulose, maltodextrin and mannitol; the disintegrant is selected from one or more of the following: croscarmellose sodium, sodium starch glycolate, calcium carboxymethylcellulose, sodium carboxymethylcellulose, cross-linked polyvinylpyrrolidone, polyvinylpyrrolidone, alginic acid, sodium alginate, pregelatinized starch, guar gum, clays and ion exchange resins; the surfactant is selected from the following: sodium lauryl sulphate, polysorbates, polyethylene polyoxypropylene polymers, polyoxylethylene stearates, dioctyl sodium sulfosuccinate, polyoxyethylene sorbitan fatty acid esters, polyoxyethylene $C_{1-4}$-alkyl ethers, sucrose monoesters and lanolin esters and ethers; and the lubricant is selected from the following: magnesium, aluminium or calcium stearate, stearic acid, sodium stearyl fumarate, talc, sodium benzoate, glyceryl mono fatty acid, polyethylene glycol, hydrogenated cotton seed oil, castor seed oil and sucrose esters.

In particular, a stable pharmaceutical composition according to this invention can comprise:
a) the compound of formula I as defined above, or a pharmaceutically acceptable salt, solvate, hydrate or morphological form thereof,
b) one or more excipients selected from the group consisting of lactose, maize starch, pregelatinised starch, calcium hydrogen phosphate and microcrystalline cellulose,
c) polyvinylpyrrolidone,
d) sodium starch glycolate,
e) a surfactant, and
f) a lubricant.

More particularly, a stable pharmaceutical composition according to this invention can comprise:
a) the compound of formula I as defined above, or a pharmaceutically acceptable salt, solvate, hydrate or morphological form thereof, in a total amount of up to 50% in weight based on the total weight of the pharmaceutical composition (e.g. in an amount from 1 to 50%, notably from 5 to 30% and in particular from 10 to 20% in weight based on the total weight of the pharmaceutical composition),
b) one or more excipients selected from the group consisting of lactose, maize starch, pregelatinised starch, calcium hydrogen phosphate and microcrystalline cellulose, in a total amount of 10 to 95% in weight based on the total weight of the pharmaceutical composition (e.g. in an amount from 30 to 90%, notably from 50 to 80% and in particular from 60 to 75% in weight based on the total weight of the pharmaceutical composition),
c) polyvinylpyrrolidone, in a total amount of up to 20% in weight based on the total weight of the pharmaceutical composition (e.g. in an amount from 0.5 to 10%, notably from 1 to 5% and in particular from 2 to 4% in weight based on the total weight of the pharmaceutical composition),
d) sodium starch glycolate, in a total amount of up to 30% in weight based on the total weight of the pharmaceutical composition (e.g. in an amount from 0.5 to 20%, notably from 1 to 10% and in particular from 2 to 6% in weight based on the total weight of the pharmaceutical composition),
e) a surfactant, in a total amount of up to 7% in weight based on the total weight of the pharmaceutical composition (e.g. in an amount from 0.01 to 5%, notably from 0.05 to 1% and in particular from 0.1 to 0.5% in weight based on the total weight of the pharmaceutical composition), and
f) a lubricant, in a total amount of up to 10% in weight based on the total weight of the pharmaceutical composition (e.g. in an amount from 0.05 to 5%, notably from 0.1 to 2% and in particular from 0.25 to 1.5% in weight based on the total weight of the pharmaceutical composition).

For example, a stable pharmaceutical composition according to this invention can comprise:
a) the compound of formula I as defined above, or a pharmaceutically acceptable salt, solvate, hydrate or morphological form thereof, in a total amount of up to 50% in weight based on the total weight of the pharmaceutical composition (e.g. in an amount from 1 to 50%, notably from 5 to 30% and in particular from 10 to 20% in weight based on the total weight of the pharmaceutical composition),
b) lactose or lactose monohydrate in a total amount of 10 to 75% in weight based on the total weight of the pharmaceutical composition (e.g. in an amount from 30 to 70%, notably from 45 to 65% and in particular from 52 to 60% in weight based on the total weight of the pharmaceutical composition)
c) microcrystalline cellulose, in a total amount of 0 to 20% in weight based on the total weight of the pharmaceutical composition (e.g. in an amount from 1 to 10%, notably from 2 to 8% and in particular from 4 to 6% in weight based on the total weight of the pharmaceutical composition),
d) polyvinylpyrrolidone, in a total amount of up to 20% in weight based on the total weight of the pharmaceutical composition (e.g. in an amount from 0.5 to 10%, notably from 1 to 5% and in particular from 2 to 4% in weight based on the total weight of the pharmaceutical composition),
e) sodium starch glycolate, in a total amount of up to 30% in weight based on the total weight of the pharmaceutical composition (e.g. in an amount from 0.5 to 20%, notably from 1 to 10% and in particular from 2 to 6% in weight based on the total weight of the pharmaceutical composition),
f) a surfactant, in a total amount of up to 7% in weight based on the total weight of the pharmaceutical composition (e.g. in an amount from 0.01 to 5%, notably from 0.05 to 1% and in particular from 0.1 to 0.5% in weight based on the total weight of the pharmaceutical composition), and
g) a lubricant, in a total amount of up to 10% in weight based on the total weight of the pharmaceutical composition (e.g. in an amount from 0.05 to 5%, notably from 0.1 to 2% and in particular from 0.25 to 1.5% in weight based on the total weight of the pharmaceutical composition).

A pharmaceutical composition according to this invention can notably comprise:
a) the compound of the formula I as defined above, or a pharmaceutically acceptable salt, solvate, hydrate or morphological form thereof,
b) lactose or lactose monohydrate,
c) microcrystalline cellulose,
d) polyvinylpyrrolidone,
e) sodium starch glycolate,
f) a surfactant, and
g) a lubricant.

According to a preferred embodiment of the compositions mentioned above, the surfactant is a polysorbate.

According to another preferred embodiment of the compositions mentioned above, the lubricant is magnesium stearate.

Optionally, the stable pharmaceutical composition of this invention may also contain a glidant. The present invention therefore further provides stable pharmaceutical compositions, comprising:
a) the compound of formula I, or a pharmaceutically acceptable salt, solvate, hydrate or morphological form thereof,
b) a filler,
c) a disintegrant,
d) a surfactant,
e) a glidant, and
f) a lubricant.

Fillers according to the invention include but are not restricted to one or more of the following: lactose, maize starch, pregelatinized starch, dibasic calcium phosphate dihydrate ($CaHPO_4.2H_2O$), microcrystalline cellulose, maltodextrin and mannitol. Preferably, lactose with microcrystalline cellulose, lactose with maize starch, pregelatinized starch with microcrystalline cellulose, or dibasic calcium phosphate dihydrate with microcrystalline cellulose are used. Also preferred is lactose monohydrate (e.g. Pharmatose® 200 Mesh) with microcrystalline cellulose (e.g. Avicel® PH101).

Disintegrants according to the invention include but are not restricted to one or more of the following: croscarmellose sodium, sodium starch glycolate, calcium carboxymethylcellulose (CMC-Ca), sodium carboxymethylcellulose CMC-Na, cross-linked polyvinylpyrrolidone (e.g. Crospovidone (PVP XL; Polyplasdone, commercially available from the ISP company or Kollidon® XL from BASF)), polyvinylpyrrolidone (PVP), alginic acid, sodium alginate, pregelatinized starch, guar gum, clays and ion exchange resins. Preferably, sodium starch glycolate is used as disintegrant, or a combination of sodium starch glycolate and PVP.

Surfactant according to the invention include but are not restricted to one or more of the following: sodium lauryl sulphate, polysorbates (commercially available as Tween®), polyethylene polyoxypropylene polymers (Pluronic F65), polyoxylethylene stearates (MYRJ), dioctyl sodium sulfosuccinate, polyoxyethylene sorbitan fatty acid esters (commercial available from Nikko Chemicals), polyoxyethylene $C_{1-4}$-alkyl ethers, sucrose monoesters and lanolin esters and ethers. Preferably, sodium lauryl sulphate is used as surfactant.

A polysorbate included in a composition according to the present invention will have a mean polymerisation degree of from 20 to 100 monomer units (preferably about 80), and may for example be polysorbate 80. Preferably also, the polysorbate should be vegetable-derived.

Glidants according to the invention include but are not restricted to one or more of the following: silica; colloidal silicon dioxide, e.g. colloidal silica anhydrous (e.g. Aerosil® 200), magnesium trisilicate, powdered cellulose, starch and talc. Preferably, colloidal silicone dioxide is used.

Lubricants according to the invention include but are not restricted to one or more of the following: Mg-, Al- or Ca-stearate, stearic acid, sodium stearyl fumarate, talc, sodium benzoate, a glyceryl mono fatty acid, e.g. having a molecular weight of from 200 to 800 Daltons (e.g. glyceryl monostearate (e.g. from Danisco, UK)), glyceryl dibehenate (e.g. CompritolAT0888™, Gattefosse France), glyceryl palmito-stearic ester (e.g. Precirol™, Gattefossé France), polyethylene glycol (PEG, BASF), hydrogenated cotton seed oil (Lubitab, Edward Mendell Co Inc.), castor seed oil (Cutina H R, Henkel) and sucrose esters (Surfhope S E, Mitsubishi-Kagaku Foods Co.). Preferably, magnesium stearate is used.

It will be appreciated that any given excipient may serve more than one function e.g. as filler, disintegrant, surfactant, glidant, and/or lubricant.

Optionally, the stable pharmaceutical composition of this invention (whether containing a glidant or not) may also contain tartaric acid.

Lactose as available from commercial suppliers is used for the present invention, preferably Lactose-monohydrate (such as Pharmatose® 200M from DMV International) is used for the present invention.

Maize starch, as available from commercial suppliers is used for the present invention, preferably maize starch from Roquette.

Pregelatinised starch as available from commercial suppliers is used for the present invention, preferably Starch 1500 (from Colorcon).

Dibasic calcium phosphate dihydrate as available from commercial suppliers is used for the present invention, preferably dibasic calcium phosphate dihydrate in an unmilled form, such as Calipharm A or A-Tab.

Microcrystalline cellulose as available from commercial suppliers is used for the present invention, preferably Avicel PH101 from FMC international.

Polyvinylpyrrolidone (PVP), as available from commercial suppliers is used for the present invention, preferably polyvinylpyrrolidone from BASF.

Sodium starch glycolate, as available from commercial suppliers is used for the present invention, preferably sodium starch glycolate from Roquette.

Sodium lauryl sulphate, as available from commercial suppliers is used for the present invention, preferably sodium lauryl sulphate from Ellis & Everard.

Colloidal silicon dioxide, as available from commercial suppliers is used for the present invention, preferably Aerosil from Degussa AG.

Magnesium stearate, as available from commercial suppliers is used for the present invention, preferably Magnesium stearate from Peter Greven.

The term "$C_{1-4}$-alkyl", alone or in combination with other groups, means a straight-chain or branched-chain alkyl group with 1 to 4 carbon atoms. Examples of straight-chain and branched $C_1$-$C_4$ alkyl groups are methyl, ethyl, propyl, isopropyl, butyl, sec-butyl, isobutyl, tert-butyl.

The term "about" placed before a numerical value "X" refers in the current application to an interval extending from X minus 10% of X to X plus 10% of X, and preferably to an interval extending from X minus 5% of X to X plus 5% of X.

The expression pharmaceutically acceptable salts encompasses either salts with inorganic acids or organic acids like hydrochloric or hydrobromic acid, sulfuric acid, phosphoric acid, citric acid, formic acid, acetic acid, maleic acid, tartaric acid, benzoic acid, methanesulfonic acid, p-toluenesulfonic acid, and the like that are non toxic to living organisms or in case the compound of formula (I) is acidic in nature with an inorganic base like an alkali or earth alkali base, e.g. sodium hydroxide, potassium hydroxide, calcium hydroxide and the like.

The expression ww % refers to a percentage by weight compared to the total weight of the composition considered.

In a preferred embodiment of the invention the pharmaceutical compositions comprise:
a filler which is selected from one or more of the following: lactose, maize starch, pregelatinized starch, dibasic calcium phosphate dihydrate ($CaHPO_4.2H_2O$) and microcrystalline cellulose, maltodextrin and mannitol; a disintegrant which is selected from one or more of the following: croscarmellose sodium, sodium starch glycolate, CMC-Ca, CMC-Na, cross-linked PVP, PVP, alginic acid, sodium alginate, pregelatinized starch, guar gum, clays and ion exchange resins; a surfactant which is selected from the following: sodium lauryl sulphate, polysorbates, polyethylene polyoxypropylene polymers, polyoxylethylene stearates and dioctyl sodium sulfosuccinate, polyoxyethylene sorbitan fatty acid esters, polyoxyethylene $C_{1-4}$-alkyl ethers, sucrose monoesters and lanolin esters and ethers; a glidant which is selected from the following: silicon dioxide, colloidal silica, magnesium trisilicate, powdered cellulose, starch and talc; a lubricant which is selected from the following: Mg-, Al- or Ca-stearate, stearic acid, sodium stearyl fumarate, talc, sodium benzoate, glyceryl mono fatty acid, polyethylene glycol, hydrogenated cotton seed oil, castor seed oil and sucrose esters.

In another preferred embodiment of the invention the pharmaceutical compositions comprise
   a) a mixture of at least one or more of the following excipients selected from lactose, maize starch, pregelatinised starch, calcium hydrogen phosphate and microcrystalline cellulose,
   b) polyvinylpyrrolidone,
   c) sodium starch glycolate,
   d) sodium lauryl sulphate,
   e) colloidal silicon dioxide, and
   f) magnesium stearate.

In a further preferred embodiment of the invention, the pharmaceutical composition, comprise
   a) a mixture of at least one or more of the following excipients selected from Lactose, Maize starch, Starch 1500, Calipharm A and Avicel PH101,
   b) polyvinylpyrrolidone,
   c) sodium starch glycolate,
   d) sodium lauryl sulphate,
   e) Aerosil, and
   f) magnesium stearate.

In another preferred embodiment of the invention the pharmaceutical compositions comprise
   a) the compound of formula I, or pharmaceutically acceptable salts, solvates, hydrates or morphological forms thereof, in a total amount of up to 50% in weight based on the total weight of the pharmaceutical composition,
   b) a mixture of at least one or more of a filler in a total amount of 10-95% in weight based on the total weight of the pharmaceutical composition,
   c) polyvinylpyrrolidone in a total amount of up to 20% in weight based on the total weight of the pharmaceutical composition,
   d) sodium starch glycolate in a total amount of up to 30% in weight based on the total weight of the pharmaceutical composition,
   e) a surfactant in a total amount of up to 7% in weight based on the total weight of the pharmaceutical composition,
   f) a glidant in a total amount of up to 5% in weight based on the total weight of the pharmaceutical composition, and
   g) a lubricant in a total amount of up to 10% in weight based on the total weight of the pharmaceutical composition,
whereby the total ww % of the pharmaceutical composition is 100.

In a further preferred embodiment of the invention, the pharmaceutical composition, comprise
   a) the compound of formula I, or pharmaceutically acceptable salts, solvates, hydrates or morphological forms thereof, in a total amount of up to 50% in weight based on the total weight of the pharmaceutical composition,
   b) a mixture of at least one or more of a filler in a total amount of 30-85% in weight based on the total weight of the pharmaceutical composition,
   c) polyvinylpyrrolidone in a range of a total amount of 2 to 10% in weight based on the total weight of the pharmaceutical composition,
   d) sodium starch glycolate in a total amount of up to 10% in weight based on the total weight of the pharmaceutical composition,
   e) a surfactant in a total amount of up to 3% in weight based on the total weight of the pharmaceutical composition,
   f) a glidant in a total amount of up to 2.5% in weight based on the total weight of the pharmaceutical composition, and
   g) a lubricant in a total amount of up to 7% in weight based on the total weight of the pharmaceutical composition,
whereby the total ww % of the pharmaceutical composition is 100.

In another preferred embodiment of the invention the pharmaceutical compositions comprise
   a) the compound of formula I, or pharmaceutically acceptable salts, solvates, hydrates or morphological forms thereof, in a total amount of up to 50% in weight based on the total weight of the pharmaceutical composition,
   b) a mixture of at least one or more of a filler in a total amount of 30-85% in weight based on the total weight of the pharmaceutical composition,
   c) polyvinylpyrrolidone in a range of a total amount of 2 to 5% in weight based on the total weight of the pharmaceutical composition,
   d) sodium starch glycolate in a total amount of up to 5% in weight based on the total weight of the pharmaceutical composition,
   e) a surfactant in a total amount of up to 3% in weight based on the total weight of the pharmaceutical composition,
   f) a glidant in a total amount of up to 1% in weight based on the total weight of the pharmaceutical composition, and
   g) a lubricant in a total amount of up to 3% in weight based on the total weight of the pharmaceutical composition,
whereby the total ww % of the pharmaceutical composition is 100.

The pharmaceutical compositions or pharmaceutically acceptable salts, solvates, hydrates or morphological forms thereof, according to the invention, may be used as a medicament.

The pharmaceutical compositions or pharmaceutically acceptable salts, solvates, hydrates or morphological forms thereof, according to the invention, may be used for the preparation of a medicament, for use in the treatment of pulmonary arterial hypertension (PAH).

Reference is made to the extensive literature on the subject for these and other pharmaceutically acceptable excipients and procedures mentioned herein, see in particular Handbook of Pharmaceutical Excipients, Third Edition, edited by Arthur H. Kibbe, American Pharmaceutical Association, Washington, USA and Pharmaceutical Press, London; and Lexikon der Hilfsstoffe für Pharmazie, Kosmetik and angrenzende Gebiete edited by H. P. Fiedler, 4th Edition, Edito Cantor, Aulendorf and earlier editions.

According to the present invention, the amount of compound of formula I, or pharmaceutically acceptable salts, solvates, hydrates or morphological forms thereof, may be a total amount of up to 90% in weight based on the total weight of the pharmaceutical composition. Preferably, the amount of compound of formula I, or pharmaceutically acceptable salts, solvates, hydrates or morphological forms thereof, may be a total amount of up to 50% in weight based on the total weight of the pharmaceutical composition. More preferably, the amount of compound of formula I, or pharmaceutically acceptable salts, solvates, hydrates or morphological forms thereof, will be from 1 to 50%, notably from 5 to 30% and in particular from 10 to 20% in weight based on the total weight of the pharmaceutical composition.

According to the present invention, the amount of filler may vary within a range of 10 to 95%, in particular 30 to 85% and more particularly 30 to 50% in weight based on the total weight of the pharmaceutical composition.

The amount of disintegrant may vary from 1 to 20%, preferably from 2 to 10% (e.g. from 3 to 8%) and notably from 2 to 5% in weight based on the total weight of the pharmaceutical composition. For example, the composition may contain 2 to 4% (e.g. 3%) disintegrant in weight based on the total weight of the pharmaceutical composition.

The amount of surfactant may vary from 0.01 to 7%, preferably from 0.1 to 3% and in particular from 0.1 to 1% in weight based on the total weight of the pharmaceutical composition.

The amount of glidant, when present in composition, may vary within ranges of from 0.1 to 5%, in particular 0.1 to 2.5%, especially 0.5 to 1.0% in weight based on the total weight of the pharmaceutical composition.

The amount of lubricant may vary from 0.05 to 10%, preferably from 0.05 to 7%, most preferably from 0.1 to 3.0% and notably between 0.1 and 1% in weight based on the total weight of the pharmaceutical composition.

The amount of tartaric acid, when present in the composition, may vary from 0.1 to 10%, preferably from 1 to 10%, and most preferably from 4 to 6% in weight based on the total weight of the pharmaceutical composition.

The absolute amounts of each pharmaceutically acceptable excipient and the amounts relative to other pharmaceutically acceptable excipients are dependent on the desired properties of the tablet and can be chosen by routine experimentation.

The total weight percent of the pharmaceutical composition is 100.

A pharmaceutical composition according to the invention is considered "stable", if during a certain period of time 70%, preferably 80% and most preferably 95% of the initial content of compound of formula I, or pharmaceutically acceptable salt, solvate, hydrate or morphological form thereof, is maintained over said period of time.

The stability of the pharmaceutical composition may be tested in conventional manner, e.g. by measurement of compound of formula I and its degradation products, dissolution, friability, disintegration time, appearance and/or microscopy, e.g. after storage at 25° C. and 60% relative humidity, and/or storage at 40° C. and 75% relative humidity for defined periods of time.

An example of a dissolution test procedure is given in the experimental part following the Examples.

Preferably, the solid compositions of this invention will be stable for at least 6 or 12 months when kept at a temperature of 5 to 50° C. More preferably, they will be stable for at least 6 or 12 months when kept at a temperature of 15 to 45 C. Most preferred, they will be stable for at least 6 or 12 months when kept at a temperature of 25 to 40° C.

In a more preferred embodiment, the pharmaceutical compositions are stable over a certain period of time such as 1 year, and preferably 2 years. More preferably, the pharmaceutical compositions are stable for 3 years.

The content of compound of formula I and its degradation products in the capsules or tablets was evaluated via HPLC.

The pharmaceutical composition may be formulated as capsule and tablet. For example a batch size of 1625 g (6500 capsules) of 1 mg dosage strength may be prepared as follows:

|  | Material (Chemical name) | Function | Percentage Formula (% w/w) | Unit Dose (mg) | For 6500 capsules (g) |
|---|---|---|---|---|---|
| Intra-granular | Compound of formula I | Active | 0.40 | 1.00 | 6.5 |
|  | Pregelatinized maize starch, EP/BP/NF | Diluent | 73.30 | 183.25 | 1191.125 |
|  | Microcrystalline cellulose, EP | Diluent/disintegrant | 10.00 | 25.00 | 162.500 |
|  | Sodium starch glycollate, EP | Disintegrant | 2.00 | 5.00 | 32.500 |
|  | Sodium lauryl sulphate, EP/NF | Surfactant | 1.00 | 2.50 | 16.250 |
| Extra-granular | Microcrystalline cellulose, EP | Diluent/disintegrant | 10.00 | 25.00 | 162.500 |
|  | Sodium starch glycollate, EP | Disintegrant | 2.00 | 5.00 | 32.500 |
|  | Colloidal silicone dioxide, EP/NF | Glidant | 0.30 | 0.75 | 4.875 |
|  | Magnesium stearate, EP/BP | Lubricant | 1.00 | 2.50 | 16.250 |
|  | Total |  | 100.000 | 250.00 | 1625.00 |

The intragranular materials were pre-mixed in a high shear mixer e.g. a Diosna, (6 L bowl) for 5 minutes. About 731-893 g of water at a rate of 65 g/minute was added to the intra-granular materials whilst mixing until suitable granules were formed. The intra-granular materials were further mixed for 2 minutes. They were then dried in a fluid bed dryer with an inlet air temperature of 60° C. until the loss on drying of the granules were 6-9% w/w. The granules were then passed through a co-mill fitted with a 813 µm screen. All the extra-granular materials except magnesium stearate were passed through a 1000 µm screen and were mixed with the granules for 25 minutes at 25 rpm in a 10 L Pharmatech double cone shell mixer. The magnesium stearate was screened through a 500 µm sieve and added to the rest of the powder mixture in the mixer and mixed for a further 3 minutes.

The powder was then filled in a size "0", white-opaque hard gelatine capsules.

In one aspect of the invention one or more lubricants may be sprayed on the material contacting surfaces of pressing tools, e.g. punches and/or dies, of the tabletting machine before compression.

The capsules may vary in size e.g. size 1 to "00".

According to the invention, tablets may also be produced. The tablets may vary in shape and be, for example, round, oval, oblong, cylindrical, clover-shaped or any other suitable shape.

In an embodiment of the invention the tablets obtained are clover shaped or round. The edges of the tablets may be beveled or rounded. In another embodiment, the tablets are clover shaped with beveled edges. The tablets according to the invention may be scored or engraved.

The tablet according to the invention may also be clover-shaped, quadrisected with beveled edges. It may have a diameter ranging between 5 and 15 mm (for example a diameter of 5 to 8 mm such as a diameter of 6 mm), notably a diameter ranging between 8 and 15 mm, and in particular a diameter ranging between 9 and 11 mm Its thickness (before coating, if a coating pellicle is applied on the tablet) is ranging from 2.5 to 4.5 mm, preferably between 2.9 and 3.9 mm The capsules and tablets of the invention may be colored and/or marked so as to impart an individual appearance and to make them instantly recognizable. The use of dyes can serve to enhance the appearance as well as to identify the tablets. Dyes suitable for use in pharmacy typically include carotinoids, iron oxides or chlorophyll. The tablets of the invention may be marked using an imprint code.

The capsules and tablets of the present invention are useful for the treatment of PAH and exhibit a good pharmacokinetic profile.

Procedures which may be used may be conventional or known in the art or based on such procedures e.g. those described in L. Lachman et al., The Theory and Practice of Industrial Pharmacy, 3rd Ed., 1986; H. Sucker et al., Pharmazeutische Technologie, Thieme, 1991; Hagers Handbuch der pharmazeutischen Praxis, 4th Ed. (Springer Verlag, 1971) and Remington's Pharmaceutical Sciences, 13th Ed., (Mack Publ., Co., 1970) or later editions.

Figure 2:
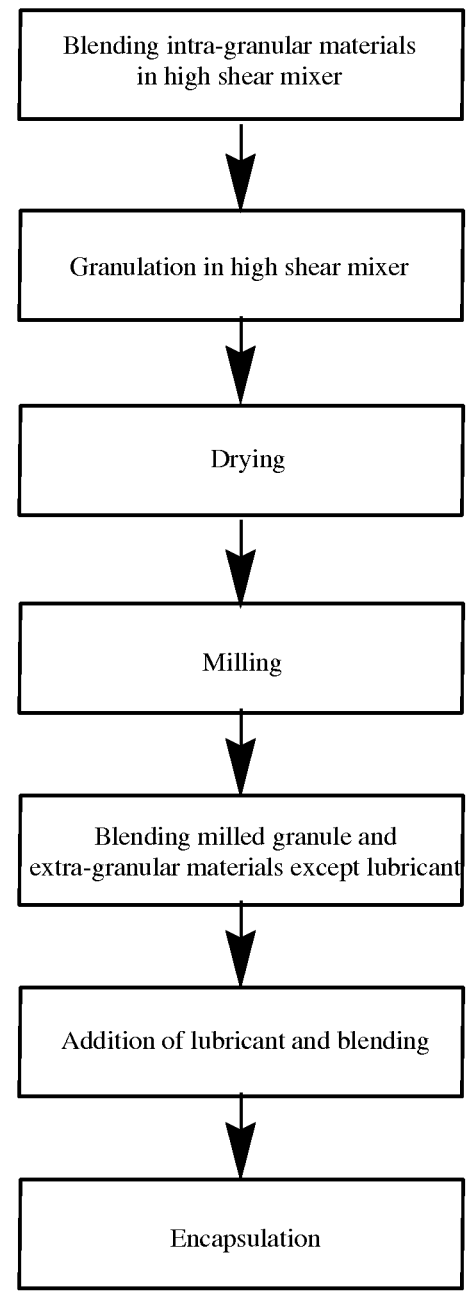
FIG. 2 shows the process for the preparation of a pharmaceutical composition in the form of capsules according to the present invention.

The process for the preparation of a pharmaceutical composition in the form of capsules according to the present invention can be carried out according to the process flow chart shown in FIG. 2.

The drying step can notably be carried out using a fluid bed dryer.

Figure 3:
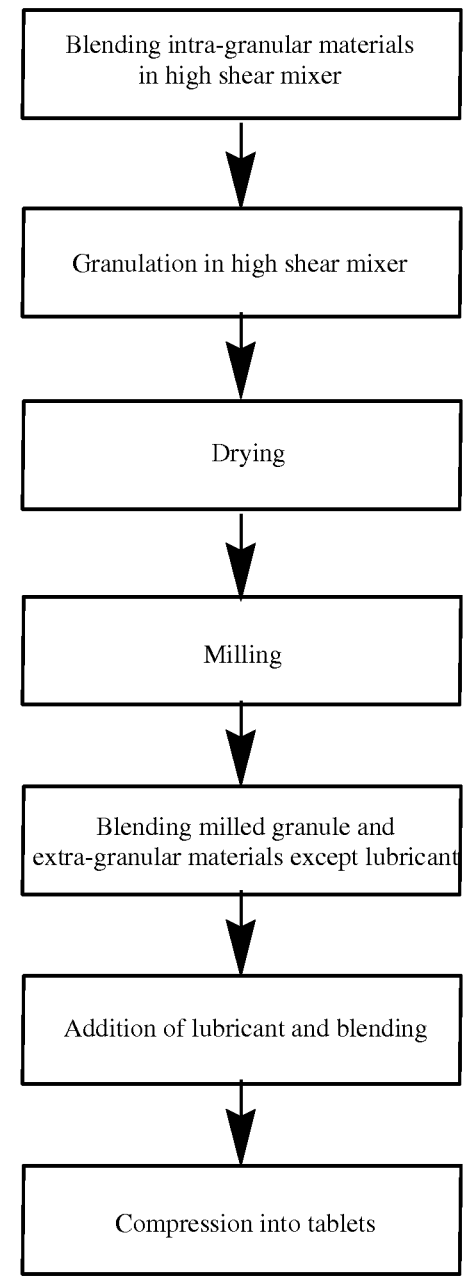
FIG. 3 shows the process for the preparation of a pharmaceutical composition in the form of tablets according to the present invention.

When the pharmaceutical composition to be prepared is in the form of tablets, the preparation process according to the present invention can be carried out according to the process flow chart shown in FIG. 3.

Two variants of this process may be carried out, one involving wet granulation (i.e. the process as shown in the flow chart above wherein some water is added to the intra-granular materials, said water being removed by the drying step), and the other involving direct compression (i.e. the process as shown in the flow chart above less the drying step, said drying step being superfluous since no water is added to the intra-granular materials).

According to a preferred variant of the process, the tablets obtained by the preparation process set out previously are coated by a protective pellicle. Said protective pellicle will notably prevent direct contact of the tablet with moisture; they may also ease imprints in the tablet.

According to this invention, the amount of coating material by weight will be from 2 to 8%, preferably from 3 to 7% and more preferably from 4 to 6% of the weight of the tablet before its coating.

The coating material making said protective pellicle will include a low water vapour permeability polymer (such as a polyvinyl alcohol (e.g. Opadry® AMB) or dimethylaminoethyl methacrylate (e.g. EUDRAGIT® E PO)). The coating material can further include a plasticizing agent (e.g. propylene glycol, triacetyne, dibutyl phthalate or dibutyl sebacate), a surfactant (e.g. sodium lauryl sulphate or a polysorbate such as Tween) and/or a lubricant/glidant (e.g. stearic acid, magnesium or calcium stearate or talc). Moreover, the coating material can also include a pigment (e.g. iron(II) oxide, iron(III) oxide or titanium oxide) to give the tablet a coloured aspect.

The following non-limitative examples illustrate the invention.

EXAMPLES

Figure 4:
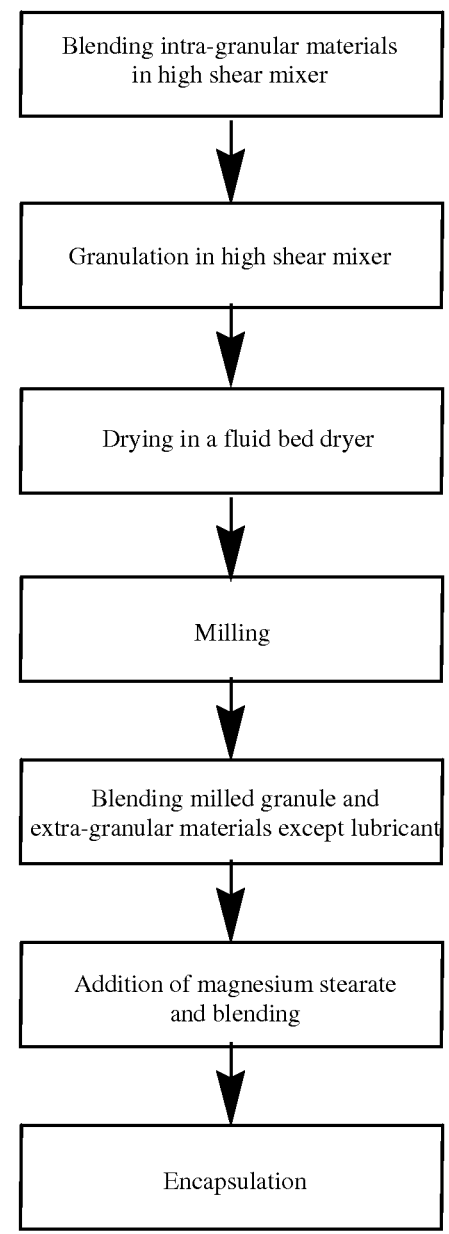
FIG. 4 shows a process summary for the preparation of the pharmaceutical composition of Examples 1-15.

The pharmaceutical compositions of Examples 1-15 were prepared according to a process summarized by the flow chart shown in FIG. 4.

Figure 5:
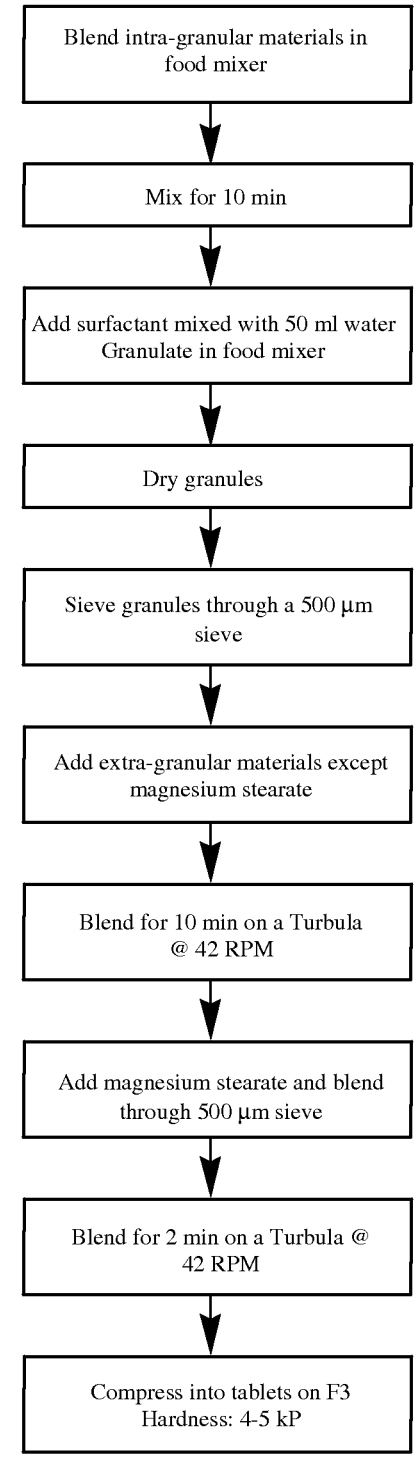
FIG. 5 shows a wet granulation process summary for the preparation of the pharmaceutical compositions of Reference Examples RE1 to RE4 and of Examples 16 to 33, 40, 41, and 43.

The pharmaceutical compositions of Reference Examples RE1 to RE4 and of Examples 16 to 33, 40, 41 and 43 were prepared by following a wet granulation process summarized by the flow chart shown in FIG. 5.

Figure 6:
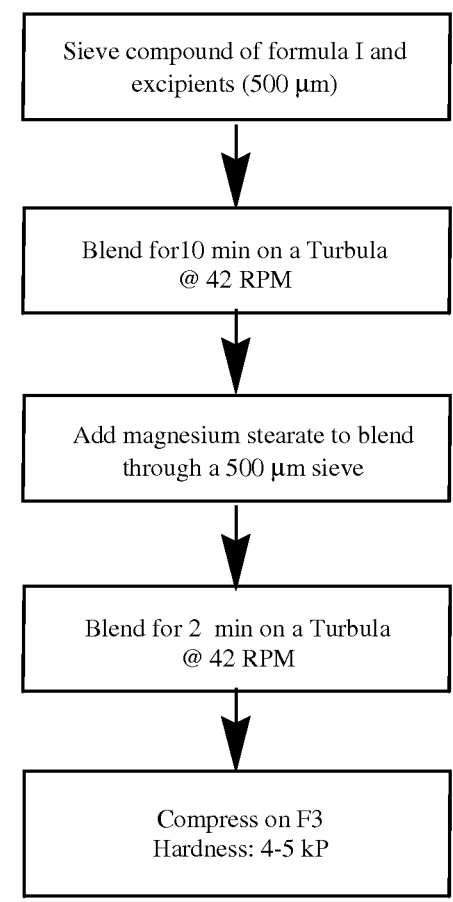
FIG. 6 shows a direct compression process summary for the preparation of the pharmaceutical compositions of Examples 34-35.

Eventually, the pharmaceutical compositions of Examples 34-35 were prepared by following a direct compression process summarized by the flow chart shown in FIG. 6. (Note that in the flow charts above, RPM means rotations per minute)

Regarding the coating of tablets with Opadry® AMB, the methodology detailed hereafter (later referred to as "general tablet coating methodology with Opadry® AMB") was used.

The coating solution for the Opadry® AMB coated tablets was obtained by preparing a 20% w/w dispersion of the Opadry® AMB (a fine white powder) in purified water in a stainless steel vessel at room temperature. The dispersion was stirred using a Heidolph stirrer equipped with a stainless steel paddle for 45 minutes before use and throughout the coating process. The coating pan was allowed to equilibrate to the set point temperature (60° C.) prior to charging with tablets. The tablets were equilibrated in the drying pan for 10 minutes prior to coating. The same temperature and airflow was used for the heating, coating and drying phases.

The parameters used for coating the tablets containing the compound of formula (I) are as follows:

| | |
|---|---|
| Coating Pan | Accelacota 24" equipped with a Manesty Flowtab unit. |
| Inlet Temperature | 60° C. |
| Exhaust Temperature | 40° C. |
| Drum Speed | 12-14 RPM |
| Spray Rate | 10 g/min increasing to 15 g/min after 60 min spraying |
| Fluid nozzle (mm) | 1.2 mm |
| Spray gun | Manesty MK-2 |
| Atomising Air Pressure | 50 psi |
| Fan Width Air Pressure | 50 psi |
| Weight of dummy tablets used to bulk out the tablet bed (g) | 7000 |
| Weight of active tablets (g) | 300 |
| ~No. of active tablets | 4300 |
| Total weight of tablet bed (g) | 7300 |

The airflow in the coating pan was not measured at the time of coating but has subsequently been measured and was found to be approximately 250 m$^3$ per hour. The film coating took between 110 and 120 minutes to complete (coating was stopped when 1460 g of the solution had been sprayed). The tablets were dried for 10 min in the pan after coating.

Regarding the coating of tablets with EUDRAGIT® E PO, the methodology detailed hereafter (later referred to as "general tablet coating methodology with EUDRAGIT® E PO") was used.

The coating trail was performed in a Lodige LHC 25. The spray gun type was an airborne spray gun Schlick 970/7-1 S75 with a nozzle diameter of 1.2 mm. As delivery system for the spraying suspension a Verder CD 70 peristaltic pump and a silicone tube with 2 mm internal diameter were used.

The coating suspension for the EUDRAGIT® E PO coated tablets was obtained as follows. Water was given in a container, the relevant quantity of sodium lauryl sulphate was added and the mixture was homogenised for 5 min using an ULTRA Turrax. Afterwards the relevant quantity of stearic acid was added in small portions and homogenised for 5-10 min. After this homogenisation period, EUDRAGIT® E PO was added slowly in small portions and homogenised for 30 min. Then the relevant quantity of magnesium stearate was prepared as 15% suspension in water by means of an ULTRA Turrax and homogenised. The magnesium stearate suspension was given to the EUDRAGIT® E PO solution. The final coating suspension was stirred continuously with conventional propeller stirrer during the process.

Reference Examples RE1 and RE2

Batch Sizes: 500 g Each

Compound of formula I tablets (250 mg)

| MATERIAL (CHEMICAL NAME) | | Reference Example RE1 | | Reference Example RE2 | |
|---|---|---|---|---|---|
| | | Percentage Formula (% w/w) | Unit Dose (mg) | Percentage Formula (% w/w) | Unit Dose (mg) |
| Intra-granular | Compound of formula I | 0.40 | 1.00 | 0.40 | 1.00 |
| | Pharmatose 200M | 76.59 | 191.475 | 75.60 | 189.00 |
| | Avicel PH101 | 5.00 | 12.50 | 5.00 | 12.50 |
| | Povidone K30 | 3.00 | 7.50 | 3.00 | 7.50 |
| | Sodium starch glycolate | 2.00 | 5.00 | 2.00 | 5.00 |
| | Sodium lauryl sulphate | 0.01 | 0.025 | 1.00 | 2.50 |
| | Water | qs | qs | qs | qs |
| Extra-granular | Avicel PH101 | 10.00 | 25.00 | 10.00 | 25.00 |
| | Sodium starch glycolate | 2.00 | 5.00 | 2.00 | 5.00 |
| | Magnesium stearate | 1.00 | 2.50 | 1.00 | 2.50 |
| | Total | 100.00 | 250.00 | 100.00 | 250.00 |

Reference Examples RE3 and RE4

Batch Sizes: 500 g Each

Compound of formula I tablets (250 mg)

| MATERIAL (CHEMICAL NAME) | | Reference Example RE3 | | Reference Example RE4 | |
|---|---|---|---|---|---|
| | | Percentage Formula (% w/w) | Unit Dose (mg) | Percentage Formula (% w/w) | Unit Dose (mg) |
| Intra-granular | Compound of formula I | 0.40 | 1.00 | 0.40 | 1.00 |
| | Pharmatose 200M | 76.60 | 191.50 | 76.55 | 191.375 |
| | Avicel PH101 | 5.00 | 12.50 | 5.00 | 12.50 |
| | Povidone K30 | 3.00 | 7.50 | 3.00 | 7.50 |
| | Sodium starch glycolate | 2.00 | 5.00 | 2.00 | 5.00 |
| | Tween 80V | 0 | 0 | 0.05 | 0.125 |
| | Water | qs | qs | qs | qs |
| Extra-granular | Avicel PH101 | 10.00 | 25.00 | 10.00 | 25.00 |
| | Sodium starch glycolate | 2.00 | 5.00 | 2.00 | 5.00 |
| | Magnesium stearate | 1.00 | 2.50 | 1.00 | 2.50 |
| | Total | 100.00 | 250.00 | 100.00 | 250.00 |

Example 1

Batch Size: 20 g

| Materials | % w/w |
|---|---|
| Compound of formula I | 40.0 |
| Pharmatose DCL11 | 28.7 |
| Starch 1500 | 25.0 |
| Sodium starch glycolate | 4.0 |
| Sodium lauryl sulphate | 1.0 |
| Colloidal silicon dioxide | 0.3 |
| Magnesium stearate | 1.0 |
| Total | 100.0 |

Examples 2 and 3

Batch Size: 625 g

| Materials | Example 2 | Example 3 |
|---|---|---|
| Compound of formula I | 0.08 | 0.08 |
| Pharmatose DCL11 | 68.62 | — |
| Starch 1500 | — | 93.62 |
| Avicel PH101 | 25.00 | — |
| Sodium starch glycolate | 4.00 | 4.00 |
| Sodium lauryl sulphate | 1.00 | 1.00 |
| Aerosil 200 | 0.30 | 0.30 |
| Magnesium stearate | 1.00 | 1.00 |
| | 100 | 100 |

Examples 4-11

| | Intra-granular materials | | | | | | | | Extra-granular materials | | | |
|---|---|---|---|---|---|---|---|---|---|---|---|---|
| % w/ Compound of formula I | % w/w Pharmatose ® 200M | % w/w Maize starch | % w/w Starch 1500 | % w/w Calipharm A | % w/w Avicel PH101 | % w/w Polyvi-nylpyr-rolidone | % w/w sodium starch glycollate | % w/w sodium lauryl sulphate | % w/w Avicel PH101 | % w/w sodium starch glycollate | % w/w Aerosil 200 | % w/w Magnesium stearate |
| 0.08 | 70.62 | — | — | — | 10.00 | 3.00 | 2.00 | 1.00 | 10.00 | 2.00 | 0.30 | 1.00 |
| 0.08 | — | — | 73.62 | — | 10.00 | — | 2.00 | 1.00 | 10.00 | 2.00 | 0.30 | 1.00 |
| 40.00 | 30.70 | — | — | — | 10.00 | 3.00 | 2.00 | 1.00 | 10.00 | 2.00 | 0.30 | 1.00 |
| 40.00 | — | — | 33.70 | — | 10.00 | — | 2.00 | 1.00 | 10.00 | 2.00 | 0.30 | 1.00 |
| 0.40 | 70.30 | — | — | — | 10.00 | 3.00 | 2.00 | 1.00 | 10.00 | 2.00 | 0.30 | 1.00 |
| 0.40 | — | — | 73.30 | — | 10.00 | — | 2.00 | 1.00 | 10.00 | 2.00 | 0.30 | 1.00 |
| 0.08 | 70.62 | 20.00 | — | — | — | 3.00 | 2.00 | 1.00 | — | 2.00 | 0.30 | 1.00 |
| 0.08 | — | — | — | 70.62 | 10.00 | 3.00 | 2.00 | 1.00 | 10.00 | 2.00 | 0.30 | 1.00 |

Example 12

Compound of formula I Capsules 0.2 mg

| | Material (Chemical name) | Function | Percentage Formula (% w/w) | Unit Dose (mg) | Typical Batch Quantity (g) |
|---|---|---|---|---|---|
| Intra-granular | Compound of formula I | Active | 0.08 | 0.20 | 0.600 |
| | Pregelatinized maize starch, EP/BP/NF | Diluent | 73.62 | 184.05 | 552.15 |
| | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Sodium lauryl sulphate, EP/NF | Surfactant | 1.00 | 2.50 | 7.50 |
| Extra-granular | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Colloidal silicone dioxide, EP/NF | Glidant | 0.30 | 0.75 | 2.25 |
| | Magnesium stearate, EP/BP | Lubricant | 1.00 | 2.50 | 7.50 |
| | Total | | 100.000 | 250.00 | 750.00 |

Example 13

Compound of formula I Capsules 1.0 mg

| | Material (Chemical name) | Function | Percentage Formula (% w/w) | Unit Dose (mg) | Typical Batch Quantity (g) |
|---|---|---|---|---|---|
| Intra-granular | Compound of formula I | Active | 0.40 | 1.00 | 3.000 |
| | Pregelatinized maize starch, EP/BP/NF | Diluent | 73.30 | 183.25 | 549.75 |
| | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Sodium lauryl sulphate, EP/NF | Surfactant | 1.00 | 2.50 | 7.50 |
| Extra-granular | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Colloidal silicone dioxide, EP/NF | Glidant | 0.30 | 0.75 | 2.25 |
| | Magnesium stearate, EP/BP | Lubricant | 1.00 | 2.50 | 7.50 |
| | Total | | 100.000 | 250.00 | 750.00 |

Example 14

Compound of formula I Capsules 10 mg

| | Material (Chemical name) | Function | Percentage Formula (% w/w) | Unit Dose (mg) | Typical Batch Quantity (g) |
|---|---|---|---|---|---|
| Intra-granular | Compound of formula I | Active | 4.00 | 10.00 | 30.00 |
| | Pregelatinized maize starch, EP/BP/NF | Diluent | 69.70 | 174.25 | 522.75 |
| | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Sodium lauryl sulphate, EP/NF | Surfactant | 1.00 | 2.50 | 7.50 |
| Extra-granular | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Colloidal silicone dioxide, EP/NF | Glidant | 0.30 | 0.75 | 2.25 |
| | Magnesium stearate, EP/BP | Lubricant | 1.00 | 2.50 | 7.50 |
| | Total | | 100.000 | 250.00 | 750.00 |

Example 15

Compound of formula I Capsules 100 mg

| | Material (Chemical name) | Function | Percentage Formula (% w/w) | Unit Dose (mg) | Typical Batch Quantity (g) |
|---|---|---|---|---|---|
| Intra-granular | Compound of formula I | Active | 40.00 | 100.00 | 300.00 |
| | Pregelatinized maize starch, EP/BP/NF | Diluent | 33.70 | 84.25 | 252.75 |
| | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Sodium lauryl sulphate, EP/NF | Surfactant | 1.00 | 2.50 | 7.50 |
| Extra-granular | Microcrystalline cellulose, EP | Diluent/disintegrant | 10.00 | 25.00 | 75.00 |
| | Sodium starch glycolate, EP | Disintegrant | 2.00 | 5.00 | 15.00 |
| | Colloidal silicone dioxide, EP/NF | Glidant | 0.30 | 0.75 | 2.25 |
| | Magnesium stearate, EP/BP | Lubricant | 1.00 | 2.50 | 7.50 |
| | Total | | 100.000 | 250.00 | 100.000 |

Examples 16-20

Batch Size: 1 kg

Compound of formula I tablets (70 mg)

| | Material (Chemical name) | Percentage Formula (% w/w) | Unit Dose (mg) |
|---|---|---|---|
| Intra-granular | Compound of formula I | 14.29 | 10.00 |
| | Pharmatose 200M | 55.51 | 38.86 |
| | Avicel PH101 | 5.00 | 3.50 |
| | Povidone K30 | 3.00 | 2.10 |
| | Sodium starch glycolate | 2.00 | 1.40 |
| | Tween 80V | 0.20 | 0.14 |
| | Water | qs | qs |
| Extra-granular | Avicel PH101 | 17.50 | 12.25 |
| | Sodium starch glycolate | 2.00 | 1.40 |
| | Magnesium stearate | 0.50 | 0.35 |
| | Total | 100.00 | 70.00 |

The following parameters were used to make the 70 mg tablets of the composition given in the table above:

| Example No. | Press setting | Mean hardness (Kp) | Mean thickness (mm) |
|---|---|---|---|
| 16 | 19 | 1.81 | 3.348 |
| 17 | 21 | 7.11 | 2.944 |
| 18 | 23 | 8.10 | 2.875 |
| 19 | 25 | 8.56 | 2.864 |
| 20 | 27 | 8.85 | 2.886 |

Examples 21-25

Batch Size: 1 kg

Compound of formula I tablets (70 mg)

| | Material (Chemical name) | Percentage Formula (% w/w) | Unit Dose (mg) |
|---|---|---|---|
| Intra-granular | Compound of formula I | 0.43 | 0.30 |
| | Pharmatose 200M | 68.37 | 47.86 |
| | Avicel PH101 | 5.00 | 3.50 |
| | Povidone K30 | 4.00 | 2.80 |

Compound of formula I tablets (70 mg)

|  | Material (Chemical name) | Percentage Formula (% w/w) | Unit Dose (mg) |
|---|---|---|---|
| | Sodium starch glycolate | 2.00 | 1.40 |
| | Tween 80V | 0.20 | 0.14 |
| | Water | qs | qs |
| Extra-granular | Avicel PH101 | 17.50 | 12.25 |
| | Sodium starch glycolate | 2.00 | 1.40 |
| | Magnesium stearate | 0.50 | 0.35 |
| | Total | 100.00 | 70.00 |

The following parameters were used to make the 70 mg tablets of the composition given in the table above (hardness and thickness parameters were measured before possible coating):

| Example No. | Press setting | Mean hardness (Kp) | Mean thickness (mm) |
|---|---|---|---|
| 21 | 19 | 1.52 | 3.339 |
| 22 | 21 | 5.77 | 3.048 |
| 23 | 23 | 6.32 | 2.989 |
| 24 | 25 | 6.88 | 3.059 |
| 25 | 27 | 6.95 | 3.006 |

Examples 26-30

Batch Size: 1 kg

Compound of formula I tablets (70 mg)

|  | Material (Chemical name) | Percentage Formula (% w/w) | Unit Dose (mg) |
|---|---|---|---|
| Intra-granular | Compound of formula I | 0.43 | 0.30 |
| | Pharmatose 200M | 68.37 | 47.86 |
| | Avicel PH101 | 5.00 | 3.50 |
| | Povidone K30 | 3.00 | 2.10 |
| | Sodium starch glycolate | 2.00 | 1.40 |
| | Tween 80V | 0.20 | 0.14 |
| | Water | qs | qs |
| Extra-granular | Avicel PH101 | 17.50 | 12.25 |
| | Sodium starch glycolate | 2.00 | 1.40 |
| | Magnesium stearate | 1.50 | 1.05 |
| | Total | 100.00 | 70.00 |

The following parameters were used to make the 70 mg tablets of the composition given in the table above (hardness and thickness parameters were measured before possible coating):

| Example No. | Press setting | Mean hardness (Kp) | Mean thickness (mm) |
|---|---|---|---|
| 26 | 19 | 2.23 | 2.774 |
| 27 | 20 | 2.53 | 2.734 |
| 28 | 21 | 2.88 | 2.713 |
| 29 | 22 | 3.30 | 2.699 |
| 30 | 23 | 3.51 | 2.657 |

Example 31

Batch Size: 500 g 250 mg tablets containing 1 mg of compound of formula I were prepared with the composition indicated in the table hereafter, using parameters similar to those of Examples 16-30 above:

Compound of formula I tablets (250 mg)

|  | Material (Chemical name) | Percentage Formula (% w/w) | Unit Dose (mg) |
|---|---|---|---|
| Intra-granular | Compound of formula I | 0.40 | 1.00 |
| | Starch 1500 | 74.60 | 186.50 |
| | Avicel PH101 | 10.00 | 25.00 |
| | Sodium starch glycolate | 2.00 | 5.00 |
| | Water | qs | qs |
| Extra-granular | Avicel PH101 | 10.00 | 25.00 |
| | Sodium starch glycolate | 2.00 | 5.00 |
| | Magnesium stearate | 1.00 | 2.50 |
| | Total | 100.00 | 250.00 |

Example 32

Batch Size: 500 g 70 mg tablets containing 1 mg of compound of formula I and having a mean hardness of 4 kP were prepared with the composition indicated in the table below, using parameters similar to those of Examples 16-30 above:

Compound of formula I tablets (70 mg)

|  | Material (Chemical name) | Percentage Formula (% w/w) | Unit Dose (mg) |
|---|---|---|---|
| Intra-granular | Compound of formula I | 1.43 | 1.00 |
| | 200M lactose | 70.86 | 49.60 |
| | Maize starch | 20.00 | 14.00 |
| | Povidone K30 | 3.00 | 2.10 |
| | Sodium starch glycolate | 2.00 | 1.40 |
| | Tween 80V | 0.14 | 0.10 |
| | Water | qs | qs |
| Extra-granular | Sodium starch glycolate | 2.00 | 1.40 |
| | Magnesium stearate | 0.57 | 0.40 |
| | Total | 100.00 | 70.00 |

Example 33

Batch Size: 500 g 70 mg tablets containing 1 mg of compound of formula I were prepared with the composition indicated in the table below, using parameters similar to those of Examples 16-30 above:

Compound of formula I tablets (70 mg)

|  | Material (Chemical name) | Percentage Formula (% w/w) | Unit Dose (mg) |
|---|---|---|---|
| Intra-granular | Compound of formula I | 1.40 | 0.98 |
| | 200M lactose | 62.50 | 43.75 |
| | Avicel PH101 | 5.00 | 3.50 |
| | Povidone K30 | 3.00 | 2.10 |
| | Sodium starch glycolate | 2.00 | 1.40 |

-continued

| | Compound of formula I tablets (70 mg) | | |
|---|---|---|---|
| | Material (Chemical name) | Percentage Formula (% w/w) | Unit Dose (mg) |
| | Tween 80V | 0.10 | 0.07 |
| | Tartaric acid | 6.00 | 4.20 |
| | Water | qs | qs |
| Extra-granular | Avicel PH101 | 17.50 | 12.25 |
| | Sodium starch glycolate | 2.00 | 1.40 |
| | Magnesium stearate | 0.50 | 0.35 |
| | Total | 100.00 | 70.00 |

Example 34

Batch Size: 500 g

| Materials | Percentage Formula (% w/w) | Unit Dose (mg) |
|---|---|---|
| Compound of formula I | 1.40 | 0.98 |
| Anhydrous lactose | 71.60 | 50.12 |
| Avicel PH112 | 22.50 | 15.80 |
| Sodium starch glycolate | 4.00 | 2.80 |
| Magnesium stearate | 0.50 | 0.40 |
| Total | 100.0 | 70.00 |

Example 35

Batch Size: 500 g

| Materials | Percentage Formula (% w/w) | Unit Dose (mg) |
|---|---|---|
| Compound of formula I | 1.40 | 0.98 |
| Mannitol (SD200) | 71.60 | 50.12 |
| Avicel PH112 | 22.50 | 15.80 |
| Sodium starch glycolate | 4.00 | 2.80 |
| Magnesium stearate | 0.50 | 0.40 |
| Total | 100.0 | 70.00 |

Example 36

70 mg tablets containing 10 mg of compound of formula I made as in Example 17 above were coated using the general tablet coating methodology with Opadry® AMB mentioned above with the following particular coating parameters (NB: the quantities mentioned for the solids and coating solution are such to allow the coating of a batch of 7300 g of uncoated tablets):

| % w/w target for tablet coating | 4% |
|---|---|
| Weight of solids required to coat (g) | 292 |
| % w/w of coating solution | 20% |
| Weight of coating solution required (g) | 1460 |

Example 37

70 mg tablets containing 10 mg of compound of formula I made as in Example 17 above were coated using the general tablet coating methodology with Opadry® AMB mentioned above with the following particular coating parameters (NB: the quantities mentioned for the solids and coating solution are such to allow the coating of a batch of 7300 g of uncoated tablets):

| % w/w target for tablet coating | 6% |
|---|---|
| Weight of solids required to coat (g) | 438 |
| % w/w of coating solution | 20% |
| Weight of coating solution required (g) | 2190 |

Example 38

70 mg tablets containing 10 mg of compound of formula I made as in Example 17 above (having a diameter of 5 mm and a height of 3.1 mm) were coated using the general tablet coating methodology with EUDRAGIT® E PO mentioned above. The uncoated tablet batch size was 500 g. The following quantities of EUDRAGIT® E PO, sodium lauryl sulphate, stearic acid, magnesium stearate and water were used:

| EUDRAGIT ® E PO (g) | 26.3 |
|---|---|
| Sodium lauryl sulphate (g) | 2.6 |
| Stearic acid (g) | 3.9 |
| Magnesium stearate (g) | 9.2 |
| Water | 238.4 |

Example 39

70 mg tablets containing 0.3 mg of compound of formula I made as in Example 28 above (having a diameter of 5 mm and a height of 2.9 mm) were coated using the general tablet coating methodology with EUDRAGIT® E PO mentioned above. The uncoated tablet batch size was 600 g. The following quantities of EUDRAGIT® E PO, sodium lauryl sulphate, stearic acid and magnesium stearate were used:

| EUDRAGIT ® E PO (g) | 92.0 |
|---|---|
| Sodium lauryl sulphate (g) | 9.2 |
| Stearic acid (g) | 13.8 |
| Magnesium stearate (g) | 32.2 |
| Water | 834.3 |

Example 40

Batch Size: 1.5 kg

| | Compound of formula I tablets (70 mg) | | |
|---|---|---|---|
| | Material (Chemical name) | Percentage Formula (% w/w) | Unit Dose (mg) |
| Intra-granular | Compound of formula I | 14.29 | 10.00 |
| | Pharmatose 200M | 55.51 | 38.86 |
| | Avicel PH101 | 5.00 | 3.50 |
| | Povidone K30 | 3.00 | 2.10 |
| | Sodium starch glycolate | 2.00 | 1.40 |
| | Tween 80V | 0.20 | 0.14 |
| | Water | qs | qs |

-continued

Compound of formula I tablets (70 mg)

| | Material (Chemical name) | Percentage Formula (% w/w) | Unit Dose (mg) |
|---|---|---|---|
| Extra-granular | Avicel PH101 | 17.50 | 12.25 |
| | Sodium starch glycolate | 2.00 | 1.40 |
| | Magnesium stearate | 0.50 | 0.35 |
| | Total | 100.00 | 70.00 |

Example 41

Batch Size: 45 kg

Compound of formula I tablets (70 mg)

| | Material (Chemical name) | Percentage Formula (% w/w) | Unit Dose (mg) |
|---|---|---|---|
| Intra-granular | Compound of formula I | 14.29 | 10.00 |
| | Pharmatose 200M | 55.51 | 38.86 |
| | Avicel PH101 | 5.00 | 3.50 |
| | Povidone K30 | 3.00 | 2.10 |
| | Sodium starch glycolate | 2.00 | 1.40 |
| | Tween 80V | 0.20 | 0.14 |
| | Water | qs | qs |
| Extra-granular | Avicel PH101 | 17.50 | 12.25 |
| | Sodium starch glycolate | 2.00 | 1.40 |
| | Magnesium stearate | 0.50 | 0.35 |
| | Total | 100.00 | 70.00 |

Example 42

70 mg tablets containing 10 mg of compound of formula I made as in Example 41 above were coated using the general tablet coating methodology with Opadry® AMB mentioned above with the following particular coating parameters (NB: the quantities mentioned for the solids and coating solution are such to allow the coating of a batch of 7300 g of uncoated tablets):

| | |
|---|---|
| % w/w target for tablet coating | 4% |
| Weight of solids required to coat (g) | 292 |
| % w/w of coating solution | 20% |
| Weight of coating solution required (g) | 1460 |

The mean hardness of the tablets thus obtained was 7.7 Kp.

Example 43

Batch Size: 45 kg

Compound of formula I tablets (70 mg)

| | MATERIAL (CHEMICAL NAME) | Percentage Formula (% w/w) | Unit Dose (mg) |
|---|---|---|---|
| Intra-granular | Compound of formula I | 4.29 | 3.00 |
| | Pharmatose 200M | 65.51 | 45.86 |
| | Avicel PH101 | 5.00 | 3.50 |
| | Povidone K30 | 3.00 | 2.10 |
| | Sodium starch glycolate | 2.00 | 1.40 |

-continued

Compound of formula I tablets (70 mg)

| | MATERIAL (CHEMICAL NAME) | Percentage Formula (% w/w) | Unit Dose (mg) |
|---|---|---|---|
| | Tween 80V | 0.20 | 0.14 |
| | Water | qs | qs |
| Extra-granular | Avicel PH101 | 17.50 | 12.25 |
| | Sodium starch glycolate | 2.00 | 1.40 |
| | Magnesium stearate | 0.50 | 0.35 |
| | Total | 100.00 | 70.00 |

Example 44

70 mg tablets containing 3 mg of compound of formula I made as in Example 43 above were coated using the general tablet coating methodology with Opadry® AMB mentioned above with the following particular coating parameters (NB: the quantities mentioned for the solids and coating solution are such to allow the coating of a batch of 7300 g of uncoated tablets):

| | |
|---|---|
| % w/w target for tablet coating | 4% |
| Weight of solids required to coat (g) | 292 |
| % w/w of coating solution | 20% |
| Weight of coating solution required (g) | 1460 |

The mean hardness of the tablets thus obtained was 7.7 Kp.

Experimental Study of the Pharmaceutical Compositions of the Invention:

Stability Test:

The quantity of substances related to the compound of formula I (i.e. products coming from the degradation of the compound of formula I) that are present after a certain time of storage at 40° C. with 75% relative humidity can be determined by HPLC for the pharmaceutical compositions of the Reference Examples and Examples above.

The experimental results obtained for the compositions of Reference Examples RE1 to RE4 can be summarized by the following table (the compound of formula I used in Reference Examples RE1 to RE4 had always a purity greater than 99.5%):

| Reference Example No. | Substances related to the compound of formula I found after 15 weeks storage at 40° C. with 75% relative humidity |
|---|---|
| RE1 | 5.76% |
| RE2 | 6.20% |
| RE3 | 8.48% |
| RE4 | 5.14% |

The experimental results obtained for the composition of Example 40 can be summarized by the following table (the compound of formula I used in Example 40 had a purity greater than 99.5%):

| Time of storage | Substances related to the compound of formula I found when stored at 40° C. with 75% relative humidity |
|---|---|
| 1 month | 0.07% |
| 2 months | 0.10% |
| 3 months | 0.14% |

The experimental results obtained for the composition of Example 42 can be summarized by the following table (the compound of formula I used in Example 42 had a purity greater than 99.5%):

| Time of storage | Substances related to the compound of formula I found when stored at 40° C. with 75% relative humidity |
|---|---|
| 3 months | 0.07% |
| 6 months | 0.10% |

Finally, the experimental results obtained for the composition of Example 44 can be summarized by the following table (the compound of formula I used in Example 44 had a purity greater than 99.5%):

| Time of storage | Substances related to the compound of formula I found when stored at 40° C. with 75% relative humidity |
|---|---|
| 3 months | 0.08% |
| 6 months | 0.23% |

Dissolution Test:
 Apparatus
 The following materials are used for the dissolution test:
 Type USP apparatus 2: SOTAX AT7 Dissolution Test station or equivalent, 6×1000 ml dissolution vessels and 6 paddles.
 HPLC system Agilent 1100 with data acquisition (Chemstation Plus).
 Analysis Balance METTLER AX 205 DR
 Milli-Q gradient A10 MILLIPORE, F1KN13093 H
Working Conditions of the Apparatus
 The following conditions are used for the dissolution test:
 Dissolution apparatus:
  Temperature: 37.0±0.5° C.
  Speed: 50±2 rpm
  Volume: 900 ml
  Dissolution medium: Buffer pH=6.8 with 0.05% Tween 80
  Sampling volume: 12 ml without medium replacement
  Sampling time point(s): profile at 5, 10, 15, 30, 45, 60 min
 HPLC parameters:
  Stationary phase: EC 250/3 Nucleodur C18 gravity 3 µm (cat. No. 7600820.30)
  Column: 250 mm×3.00 mm 3 µm (Macherey-Nagel)
  Mobile phase: Isocratic
  Injected volume: 10 µl
  Column temperature: 25° C.
  Auto sampler temperature: 25° C.
  Flow rate: 0.5 ml/min
  Pressure: 149 bar
  Detection wavelength: 260 nm
  Chromatogram time: 10 min
  Mobile phase: Mix well 850 ml acetonitrile, 150 ml water and 5 ml trifluoroacetic acid. Degas before use.
Protocol
 10 l of the dissolution medium are prepared as follows: 79.85 g of $NaH_2PO_4 \cdot 2H_2O$, 69.55 g of $Na_2HPO_4$ and 5 g of Tween 80 are diluted with water to a total volume of 10 l.
 A reference standard solution of compound of formula I is prepared in duplicate. One of the reference standard solutions will be used as the working reference standard solution, and the other standard solution will be used as a control reference standard solution. A reference standard solution of compound of formula I is obtained as follows:
 55 mg of compound of formula I are weighed in a 250 ml volumetric flask and 4 ml acetonitrile are added. The mixture is sonicated for 5 minutes. After complete dissolution of the compound of formula I, dissolution medium is added to complete to 250 ml. 10.0 ml of this solution are taken by pipette into a 200 ml volumetric flask, dissolution medium is added to complete to 250 ml. The concentration of compound of formula I in the reference standard solution is thus 11 µg/ml.
 The dissolution sample solution is prepared as follows:
 900 ml of dissolution medium are transferred into each vessel of the dissolution apparatus. The dissolution medium is allowed to equilibrate for at least 30 min in the dissolution batch at 37° C.±0.5° C. A 10 mg tablet of compound of formula I is dropped into each vessel. 12 ml of the sample solution are withdrawn from each vessel at 5, 10, 15, 30, 45 and 60 min. No medium replacement is required. The sample solution is filtered without delay through a Gelman 1 µm glass fibre acrodisk syringe filter into an HPLC vial and cooled to room temperature.
 The following injection sequence is used for carrying out the HPLC analysis:
  the dissolution medium is injected once;
  the working reference standard solution is injected 6 times consecutively;
  the control reference standard solution is injected twice;
  each sample solution is injected once.
 After the six samples injections, the working reference standard solution is re-injected to ensure that the system drift is within the limit (2.0%).
 The following criteria must be met:
  The working reference standard solution is consecutively injected six times. The % RSD from the response factors (i.e. the concentration of the reference solution divided by the peak area of the reference solution) should be ≤2.0%. The overall RSD of response factor of compound of formula I in the working reference standard solution injected throughout the run should be ≤2.0%.
  The relative difference between the mean response factor of 6 injections of the working reference standard solution and the mean of 2 injections of the control reference standard solution should be ≤1.5%.
 The results can be calculated using the following formulae:

| N | Sampling time (min) | $\sum_{i=1}^{n-1} C_i V_r$ |
|---|---|---|
| 1 | 5 | 0 |
| 2 | 10 | $C_1 V_r$ |
| 3 | 15 | $(C_1 + C_2)V_r$ |
| 4 | 30 | $(C_1 + C_2 + C_3)V_r$ |
| 5 | 45 | $(C_1 + C_2 + C_3 + C_4)V_r$ |
| 6 | 60 | $(C_1 + C_2 + C_3 + C_4 + C_5)V_r$ |
| etc. | | |

$$D(\%) = \frac{C_n V_n + \sum_{i=1}^{n-1} C_i V_r}{T} \times 100$$

$$V_n = V - V_r(n-1)$$

$$C = \frac{A_{spl}}{A_{std}} \times c_{std}$$

$$C_{std} = \frac{W_{std}}{DF_{std}} \times \frac{P_{std}}{100}$$

wherein

D (%)=compound of formula I dissolved based on labeled quantity $C_n$=concentration of compound of formula I for the $n^{th}$ injection, in mg/ml V=initial volume of dissolution medium, in ml=900

$V_r$=volume of dissolution medium removed for each injection, in ml=12

$V_n$=actual volume of dissolution medium, in ml, for the $n^{th}$ injection

T=labeled quantity of compound of formula I per tablet=10 mg n=$n^{th}$ sampling $A_{spl}$=peak area of compound of formula I obtained from the sample solution $A_{std}$=peak area of compound of formula I obtained from the working reference standard solution $C_{std}$=concentration in mg/ml, of compound of formula I in the working reference standard solution $W_{std}$=weight of compound of formula I in the working reference standard solution, in mg $P_{std}$=potency of compound of formula I reference substance in %

$DF_{std}$=dilution factor of the standard solution, in ml=5'000

Results for Pharmaceutical Compositions According to the Invention:

The compositions of Examples 16-20, when tested using the protocol explained, show the dissolution profile shown in FIG. 1 (wherein the percentage dissolution (Y-axis) is represented in function of the time in min (X-axis)).

The dissolution profiles of the tablets of this invention can also be tested using the method described above after a certain time of storage at 40° C. with 75% relative humidity.

Accordingly, the dissolution profiles obtained for the tablets of Example 40 are as follows.

| Time of storage at 40° C. with 75% relative humidity | % of compound of formula I dissolved after (ranges of values found) | | | | | |
|---|---|---|---|---|---|---|
| | 5 minutes | 10 minutes | 15 minutes | 30 minutes | 45 minutes | 60 minutes |
| None | 45 (36-63) | 91 (88-96) | 102 (98-105) | 110 (105-114) | 107 (102-112) | 105 (101-109) |
| 1 month | 41 (35-48) | 87 (84-91) | 103 (95-115) | 114 (98-133) | 112 (98-129) | 111 (97-124) |
| 2 months | 40 (36-43) | 62 (58-65) | 73 (68-80) | 86 (81-92) | 90 (86-96) | 92 (86-100) |
| 3 months | 51 (49-52) | 64 (56-68) | 72 (70-75) | 82 (80-86) | 86 (84-88) | 87 (82-90) |

Furthermore, the results obtained for the tablets of Example 42 can be summarized as follows:

| Time of storage at 40° C. with 75% relative humidity | % of compound of formula I dissolved after (ranges of values found) | | | | | |
|---|---|---|---|---|---|---|
| | 5 minutes | 10 minutes | 15 minutes | 30 minutes | 45 minutes | 60 minutes |
| None | 46 (41-52) | 76 (74-79) | 86 (81-91) | 94 (89-98) | 96 (89-100) | 96 (91-100) |
| 3 months | 56 (47-66) | 83 (82-86) | 89 (83-92) | 94 (90-99) | 96 (91-99) | 96 (91-101) |
| 6 months | 61 (57-65) | 83 (79-88) | 88 (83-94) | 96 (92-101) | 96 (91-100) | 97 (92-101) |

Moreover, the results obtained for the tablets of Example 44 can be summarized as follows:

| Time of storage at 40° C. with 75% relative humidity | % of compound of formula I dissolved after (ranges of values found) | | | | | |
|---|---|---|---|---|---|---|
| | 5 minutes | 10 minutes | 15 minutes | 30 minutes | 45 minutes | 60 minutes |
| None | 45 (42-49) | 81 (78-86) | 90 (87-94) | 96 (93-100) | 98 (95-101) | 98 (96-101) |
| 3 months | 39 (35-43) | 84 (82-88) | 90 (88-92) | 94 (91-96) | 94 (92-97) | 94 (91-97) |
| 6 months | 39 (34-43) | 79 (77-83) | 86 (84-89) | 91 (87-94) | 91 (88-93) | 91 (88-93) |

The invention claimed is:

1. A pharmaceutical composition comprising:
   a) the compound of the formula I as drawn below

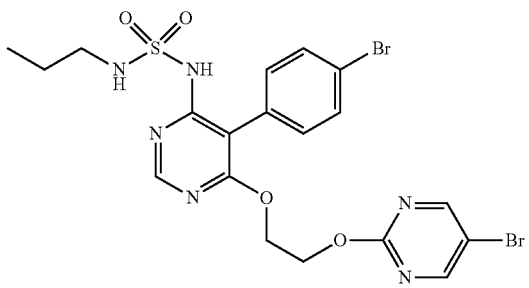

or a pharmaceutically acceptable salt, solvate, hydrate or morphological form thereof, in a total amount of 1 to 50% in weight based on the total weight of the pharmaceutical composition,
   b) filler, in an amount of 10 to 95% in weight based on the total weight of the pharmaceutical composition,
   c) disintegrant, in an amount of 1 to 20% in weight based on the total weight of the pharmaceutical composition,
   d) surfactant, in an amount from 0.1 to 1% in weight based on the total weight of the pharmaceutical composition, wherein the surfactant comprises a polysorbate, and
   e) lubricant, in an amount from 0.05 to 10% in weight based on the total weight of the pharmaceutical composition.

2. The pharmaceutical composition of claim 1, wherein the filler comprises one or more from lactose, maize starch, pregelatinized starch, dibasic calcium phosphate dihydrate (CaHPO$_4$.2H$_2$O), microcrystalline cellulose, maltodextrin and mannitol.

3. The pharmaceutical composition of claim 1, wherein the filler comprises lactose.

4. The pharmaceutical composition of claim 1, wherein the filler comprises microcrystalline cellulose.

5. The pharmaceutical composition of claim 1, wherein the filler comprises lactose and microcrystalline cellulose.

6. The pharmaceutical composition of claim 1, wherein the filler comprises maize starch.

7. The pharmaceutical composition of claim 1, wherein the filler comprises pregelatinized starch.

8. The pharmaceutical composition of claim 1, wherein the filler comprises dibasic calcium phosphate dihydrate (CaHPO$_4$.2H$_2$O).

9. The pharmaceutical composition of claim 1, wherein the filler comprises mannitol.

10. The pharmaceutical composition of claim 1, wherein the disintegrant comprises one or more from croscarmellose sodium, sodium starch glycolate, calcium carboxymethylcellulose, sodium carboxymethylcellulose, cross-linked polyvinylpyrrolidone, polyvinylpyrrolidone, alginic acid, sodium alginate, pregelatinized starch, guar gum, clays and ion exchange resins.

11. The pharmaceutical composition of claim 10, wherein the disintegrant comprises croscarmellose sodium.

12. The pharmaceutical composition of claim 10, wherein the disintegrant comprises sodium starch glycolate.

13. The pharmaceutical composition of claim 10, wherein the disintegrant comprises cross-linked polyvinylpyrrolidone.

14. The pharmaceutical composition of claim 10, wherein the disintegrant comprises polyvinylpyrrolidone.

15. The pharmaceutical composition of claim 10, wherein the disintegrant comprises pregelatinized starch.

16. The pharmaceutical composition of claim 1, wherein the polysorbate is polysorbate 80.

17. The pharmaceutical composition of claim 1, wherein the lubricant comprises one or more from magnesium stearate, aluminium stearate, calcium stearate, stearic acid, sodium stearyl fumarate, talc, sodium benzoate, a glyceryl mono fatty acid, glyceryl dibehenate, glyceryl palmitostearic ester, polyethylene glycol, hydrogenated cotton seed oil, castor seed oil and sucrose esters.

18. The pharmaceutical composition of claim 17, wherein the lubricant comprises magnesium stearate.

19. The pharmaceutical composition of claim 17, wherein the lubricant comprises aluminium stearate.

20. The pharmaceutical composition of claim 17, wherein the lubricant comprises calcium stearate.

21. The pharmaceutical composition of claim 17, wherein the lubricant comprises stearic acid.

22. The pharmaceutical composition of claim 1, which is in the form of a tablet.

23. The pharmaceutical composition of claim 10, which is in the form of a tablet.

24. The pharmaceutical composition of claim 16, which is in the form of a tablet.

25. The pharmaceutical composition of claim 17, which is in the form of a tablet.

26. A method of treating pulmonary arterial hypertension comprising the administration of a pharmaceutical composition according to claim 1 to a patient in need thereof.

27. A method of treating pulmonary arterial hypertension comprising the administration of a pharmaceutical composition according to claim 10 to a patient in need thereof.

28. A method of treating pulmonary arterial hypertension comprising the administration of a pharmaceutical composition according to claim 16 to a patient in need thereof.

29. A method of treating pulmonary arterial hypertension comprising the administration of a pharmaceutical composition according to claim 17 to a patient in need thereof.

30. A method of treating pulmonary arterial hypertension comprising the administration of a pharmaceutical composition according to claim 22 to a patient in need thereof.

31. A method of treating pulmonary arterial hypertension comprising the administration of a pharmaceutical composition according to claim 23 to a patient in need thereof.

32. A method of treating pulmonary arterial hypertension comprising the administration of a pharmaceutical composition according to claim 24 to a patient in need thereof.

33. A method of treating pulmonary arterial hypertension comprising the administration of a pharmaceutical composition according to claim 25 to a patient in need thereof.

34. A pharmaceutical composition comprising:
a) the compound of the formula I as drawn below

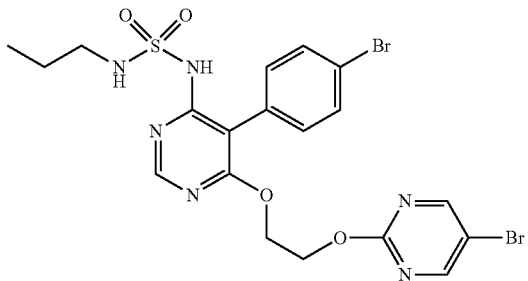

or a pharmaceutically acceptable salt, solvate, hydrate or morphological form thereof, in a total amount of 1 to 50% in weight based on the total weight of the pharmaceutical composition,
b) filler, in an amount of 10 to 95% in weight based on the total weight of the pharmaceutical composition, wherein the filler comprises one or more from lactose, maize starch, pregelatinized starch, dibasic calcium phosphate dihydrate ($CaHPO_4 \cdot 2H_2O$), microcrystalline cellulose, maltodextrin and mannitol,
c) disintegrant, in an amount of 1 to 20% in weight based on the total weight of the pharmaceutical composition, wherein the disintegrant comprises one or more from croscarmellose sodium, sodium starch glycolate, calcium carboxymethylcellulose, sodium carboxymethylcellulose, cross-linked polyvinylpyrrolidone, polyvinylpyrrolidone, alginic acid, sodium alginate, pregelatinized starch, guar gum, clays and ion exchange resins,
d) surfactant, in an amount from 0.1 to 1% in weight based on the total weight of the pharmaceutical composition, wherein the surfactant comprises a polysorbate, and
e) lubricant, in an amount from 0.05 to 10% in weight based on the total weight of the pharmaceutical composition, wherein the lubricant comprises one or more from magnesium stearate, aluminium stearate, calcium stearate, stearic acid, sodium stearyl fumarate, talc, sodium benzoate, a glyceryl mono fatty acid, glyceryl dibehenate, glyceryl palmito-stearic ester, polyethylene glycol, hydrogenated cotton seed oil, castor seed oil and sucrose esters.

35. The pharmaceutical composition of claim 34, wherein the disintegrant is sodium starch glycolate or a combination of sodium starch glycolate and polyvinylpyrrolidone.

36. The pharmaceutical composition of claim 34, wherein the surfactant is polysorbate 80.

37. The pharmaceutical composition of claim 34, wherein the lubricant comprises magnesium stearate.

38. The pharmaceutical composition of claim 34, which is in the form of a tablet.

39. The pharmaceutical composition of claim 36, which is in the form of a tablet.

40. A method of treating pulmonary arterial hypertension comprising the administration of a pharmaceutical composition according to claim 34 to a patient in need thereof.

41. A method of treating pulmonary arterial hypertension comprising the administration of a pharmaceutical composition according to claim 38 to a patient in need thereof.

42. A method of treating pulmonary arterial hypertension comprising the administration of a pharmaceutical composition according to claim 39 to a patient in need thereof.

* * * * *